Jan. 21, 1936. A. F. WATKINS Plant Pat. 163
ROSE
Filed Aug. 22, 1935
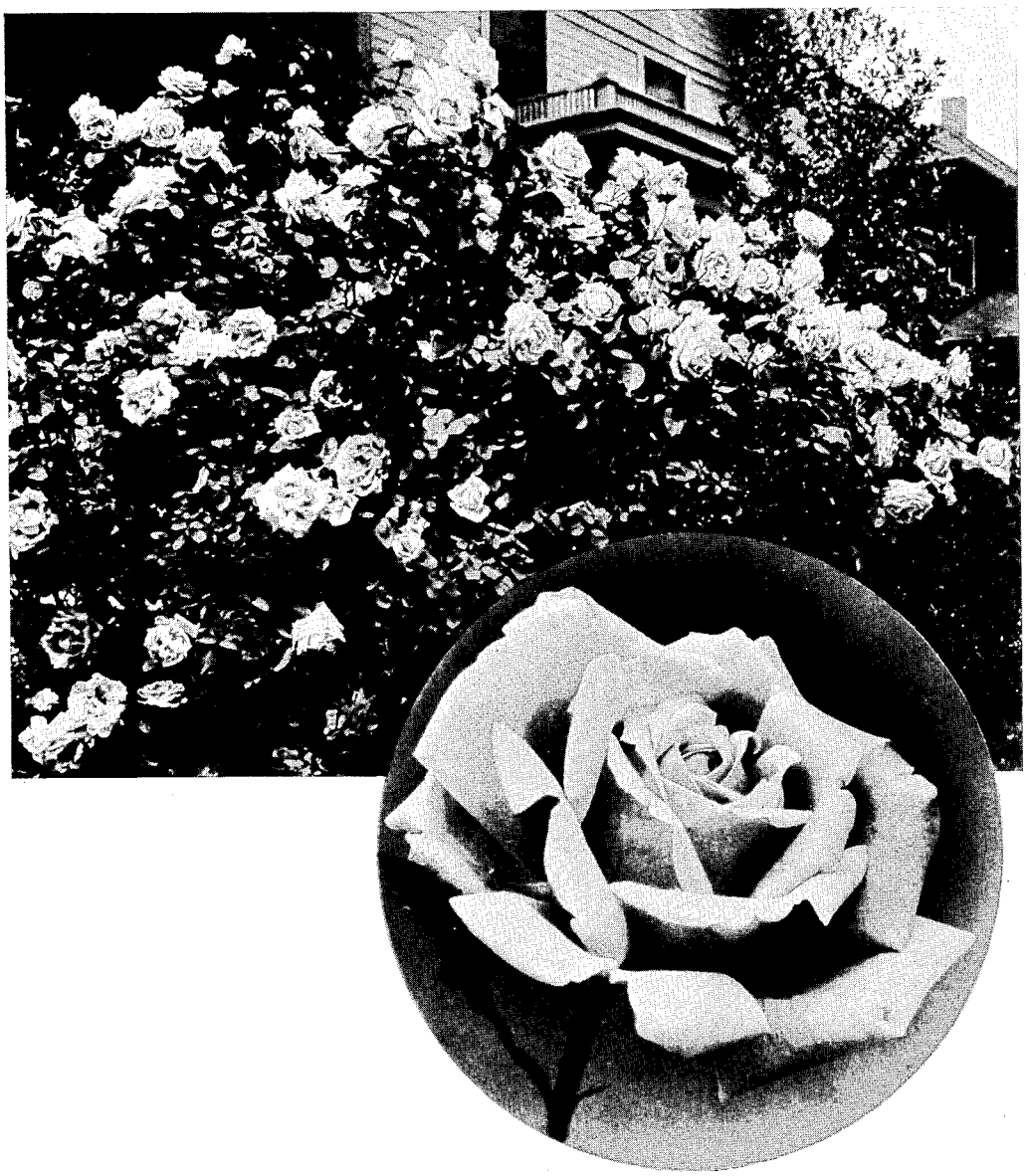
Inventor
Archibald Flint Watkins
By Robb & Robb
attorneys Patented Jan. 21, 1936

Plant Pat. 163

UNITED STATES PATENT OFFICE

163

ROSE

Archibald Flint Watkins, Tyler, Tex., assignor of one-half to Jackson & Perkins Company, Newark, N. Y., and one-half to Dixie Rose Nursery, Tyler, Tex.

Application August 22, 1935, Serial No. 37,409

1 Claim. (Cl. 47—61)

In Plant Patent No. 62 there is disclosed a new variety of hybrid tea known commercially as "Gov. Alfred E. Smith", a bush plant of vigorous and hardy characteristics.

The present discovery is a sport of this patented variety and as such is distinguished therefrom by a climbing habit. In all other respects, including the bloom, this new variety is identical with its parent variety.

The climbing habit of the new plant is found to be vigorous, inasmuch as plants reach great height in one season.

One of the important features of the present variety is found in its unusual hardiness, for its class, due primarily to its growth of hard wood with very little pith. This hardiness makes it available in the North with the large flowering "hardy" climbers.

Asexual reproduction of the present variety proves the novel climbing characteristic to be fixed.

Specific description of the new plant is unnecessary as it does not depart in any respect, except as herein mentioned, from the known parent fully disclosed in the prior patent.

I claim:

A new and distinct variety of rose plant as herein shown and described, characterized by its climbing habit and unusual hardiness for a rose of its class.

ARCHIBALD FLINT WATKINS.